US012623093B2

(12) United States Patent 
Sjolund et al.

(10) Patent No.: US 12,623,093 B2 
(45) Date of Patent: May 12, 2026

(54) CONTINUUM RADIOTHERAPY TREATMENT PLANNING

(71) Applicant: Elekta AB (publ), Stockholm (SE)

(72) Inventors: Jens Olof Sjolund, Uppsala (SE); Carl Axel Håkan Nordström, Stockholm (SE)

(73) Assignee: Elekta AB (publ), Stockholm (SE)

( * ) Notice: Subject to any disclaimer, the term of this patent is extended or adjusted under 35 U.S.C. 154(b) by 228 days.

(21) Appl. No.: 18/695,565

(22) PCT Filed: Oct. 25, 2021

(86) PCT No.: PCT/EP2021/079551
§ 371 (c)(1),
(2) Date: Mar. 26, 2024

(87) PCT Pub. No.: WO2023/072364
PCT Pub. Date: May 4, 2023

(65) Prior Publication Data
US 2024/0408410 A1 Dec. 12, 2024

(51) Int. Cl.
*A61N 5/10* (2006.01)
*G16H 20/40* (2018.01)
(Continued)

(52) U.S. Cl.
CPC ........... *A61N 5/1047* (2013.01); *A61N 5/103* (2013.01); *G16H 20/40* (2018.01); *G16H 30/40* (2018.01);
(Continued)

(58) Field of Classification Search
CPC ...... A61N 5/103; A61N 5/1047; G16H 20/40; G16H 30/40; G16H 40/63; G16H 50/20; G16H 50/50; G16H 50/70
See application file for complete search history.

(56) References Cited

U.S. PATENT DOCUMENTS 8,654,923 B2 2/2014 Luan et al.
8,835,877 B2 9/2014 Luan et al.
(Continued)

FOREIGN PATENT DOCUMENTS

WO WO-2023072364 A1 5/2023

OTHER PUBLICATIONS

"International Application Serial No. PCT/EP2021/079551, International Search Report mailed Jun. 27, 2022", 5 pgs.
(Continued)

*Primary Examiner* — Mark R Gaworecki
(74) *Attorney, Agent, or Firm* — Schwegman Lundberg & Woessner, P.A.

(57) ABSTRACT

Systems and methods are disclosed for dynamic radiotherapy treatment planning in a continuous space of computation. Example operations for generating treatment plan data for a radiotherapy treatment include: obtaining data for a radiotherapy treatment of a human subject; generating a set of radiation controls from the data for the radiotherapy treatment, with at least one of the radiation controls being based on a mapping from a continuous (e.g., infinite dimensional) computational space; converting the generated set of radiation controls to a set of treatment delivery parameters, the set of treatment delivery parameters corresponding to capabilities of a radiotherapy treatment machine; and producing treatment plan data for the radiotherapy treatment based on the set of treatment delivery parameters.

24 Claims, 9 Drawing Sheets

(51) Int. Cl.

| | | |
|---|---|---|
| *G16H 30/40* | (2018.01) | |
| *G16H 40/63* | (2018.01) | |
| *G16H 50/20* | (2018.01) | |
| *G16H 50/50* | (2018.01) | |
| G16H 50/70 | (2018.01) | |

(52) U.S. Cl.
CPC ............. *G16H 40/63* (2018.01); *G16H 50/20* (2018.01); *G16H 50/50* (2018.01); *G16H 50/70* (2018.01)

(56) References Cited

U.S. PATENT DOCUMENTS

| | | |
|---|---|---|
| 10,744,343 B2 | 8/2020 | Sjölund et al. |
| 2010/0183121 A1 | 7/2010 | Riker et al. |
| 2011/0122997 A1 | 5/2011 | Lu et al. |
| 2013/0197878 A1 | 8/2013 | Fiege et al. |
| 2015/0367145 A1 | 12/2015 | Sjolund et al. |
| 2018/0326222 A1 | 11/2018 | Otto |

OTHER PUBLICATIONS

"International Application Serial No. PCT/EP2021/079551, Written Opinion mailed Jun. 27, 2022", 5 pgs.

Ghobadi, Kimia, "Optimization methods for patient positioning in Leksell Gamma Knife R PerfexionTM", A thesis submitted in conformity with the requirements for the degree of Doctor of Philosophy Graduate Department of Mechanical and Industrial Engineering University of Toronto, (2014), 159 pages.

Langhans, Marco, et al., "Optimizing highly noncoplanar VMAT trajectories: the NoVo method", Zurich Open Repository and Archive, (2018), 17 pages.

Sjölund, J., et al., "A linear programming approach to inverse planning in Gamma Knife radiosurgery", Med. Phys. 46 (4), (Mar. 8, 2019), 12 pages.

Vandewouw, Marlee M., et al., "Robotic path-finding in inverse treatment planning for stereotactic radiosurgery with continuous dose delivery", Medical Physics 43, 4545 (2016); doi: 10.1118/1.4955177, (Aug. 2016), 14 pages.

"International Application Serial No. PCT EP2021 079551, International Preliminary Report on Patentability mailed May 10, 2024", 7 pgs.

"European Application Serial No. 21801070.0, Response to Communication Pursuant to Rules 161 and 162 EPC filed Dec. 6, 2024", 18 pgs.

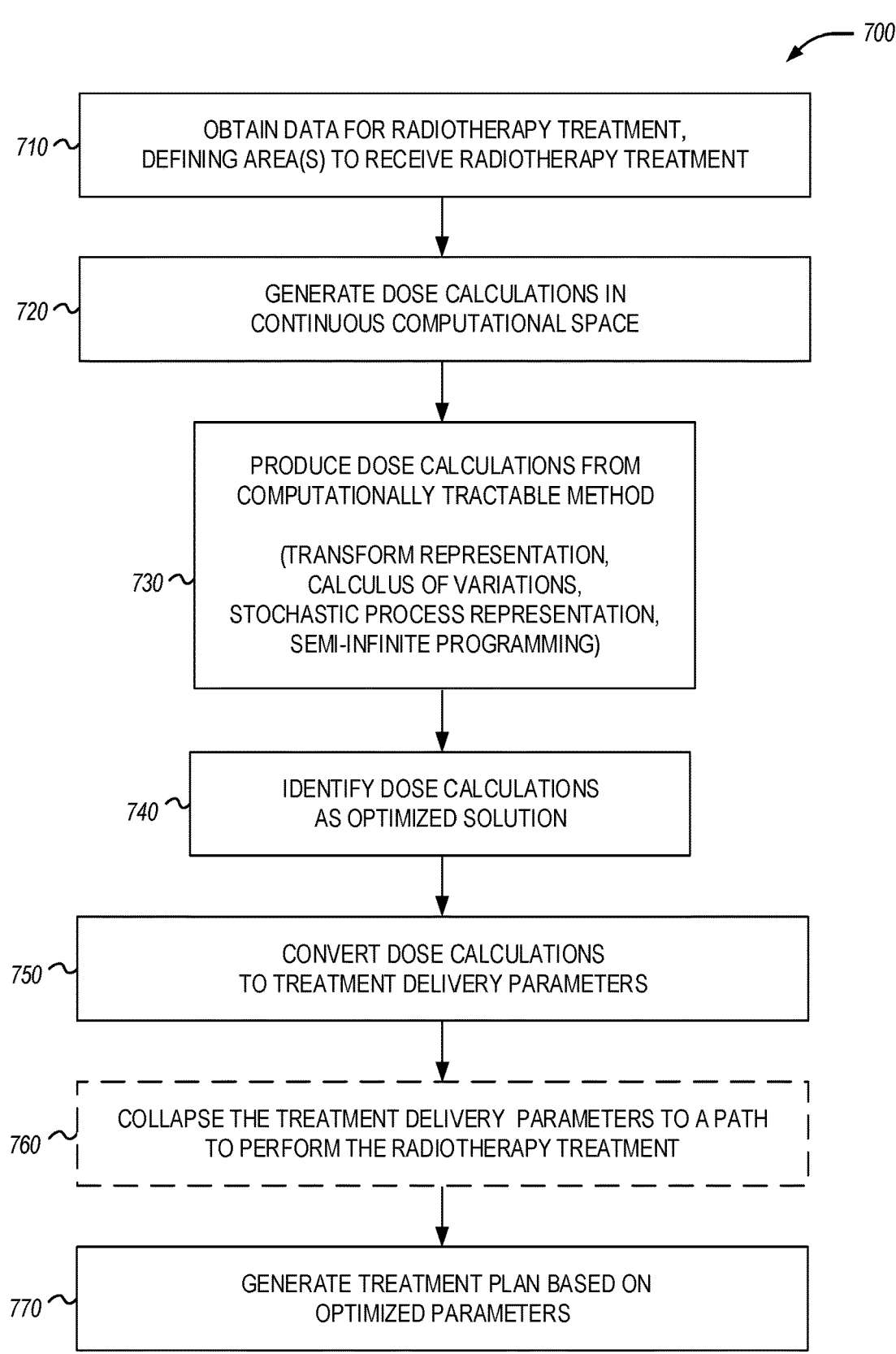

700

710 — OBTAIN DATA FOR RADIOTHERAPY TREATMENT, DEFINING AREA(S) TO RECEIVE RADIOTHERAPY TREATMENT

720 — GENERATE DOSE CALCULATIONS IN CONTINUOUS COMPUTATIONAL SPACE

730 — PRODUCE DOSE CALCULATIONS FROM COMPUTATIONALLY TRACTABLE METHOD (TRANSFORM REPRESENTATION, CALCULUS OF VARIATIONS, STOCHASTIC PROCESS REPRESENTATION, SEMI-INFINITE PROGRAMMING)

740 — IDENTIFY DOSE CALCULATIONS AS OPTIMIZED SOLUTION

750 — CONVERT DOSE CALCULATIONS TO TREATMENT DELIVERY PARAMETERS

760 — COLLAPSE THE TREATMENT DELIVERY PARAMETERS TO A PATH TO PERFORM THE RADIOTHERAPY TREATMENT

770 — GENERATE TREATMENT PLAN BASED ON OPTIMIZED PARAMETERS

*FIG. 7*

CONTINUUM RADIOTHERAPY TREATMENT PLANNING

PRIORITY APPLICATIONS

This application is a U.S. National Stage Filing under 35 U.S.C. § 371 from International Application No. PCT/EP2021/079551, filed on Oct. 25, 2021, and published as WO2023/072364 on May 4, 2023; the benefit of priority of which is hereby claimed herein, and which application and publication is hereby incorporated herein by reference in its entirety.

TECHNICAL FIELD

Embodiments of the present disclosure pertain generally to processing and optimization techniques used in connection with a radiation therapy planning and treatment system. In particular, the present disclosure pertains to the use of computationally tractable methods for continuum treatment planning and delivery in connection with planning for a radiation therapy session.

BACKGROUND

Radiation therapy (or "radiotherapy") can be used to treat cancers or other ailments in mammalian (e.g., human and animal) tissue. One such radiotherapy technique is provided using a Gamma Knife, by which a patient is irradiated by a large number of low-intensity gamma rays that converge with high intensity and high precision at a target (e.g., a tumor). Another such radiotherapy technique is provided using an accelerator, whereby a tumor is irradiated by high-energy particles (e.g., electrons, protons, ions, high-energy photons, and the like). The placement and dose of the radiation beam must be accurately controlled to ensure the tumor receives the prescribed radiation, and the placement of the beam should be such as to minimize damage to the surrounding healthy tissue, often called the organ(s) at risk (OARs).

In radiotherapy, treatment planning is typically performed in a sequential manner, where the degrees of freedom (e.g., the isocenter locations in Gamma Knife) are determined prior to solving an optimization problem. However, determining the degrees of freedom necessarily restricts the search space of the optimization, and thereby bounds the quality of treatment plans that can be found by the optimization—sometimes even to the point where no acceptable plan exists and the degrees of freedom have to be redetermined and the optimization must be re-calculated.

Some limited approaches have been proposed to improve treatment planning for the paths used to deliver treatment with a Gamma Knife. However, the resulting path that is produced by such approaches may not be fully optimized.

OVERVIEW

In some embodiments, methods, systems, and computer-readable mediums are provided for evaluations and optimizations performed on a radiotherapy treatment plan designed for a radiotherapy treatment session. An initial step in conventional treatment planning is to determine the degrees of freedom that is later used to solve an optimization problem. The following provides an expanded approach for radiotherapy treatment planning optimization by removing the initial step of determining the degrees of freedom, and instead, performing a radiotherapy treatment planning in a continuum limit as an initial step of optimization.

In various examples, operations for such evaluations and optimizations in a radiotherapy treatment planning setting include: obtaining data for a radiotherapy treatment of a human subject; generating a set of radiation controls from the data for the radiotherapy treatment, where at least one of the radiation controls is based on (e.g., defined by) a mapping from a continuous computational space; converting the generated set of radiation controls to a set of treatment delivery parameters, with the set of treatment delivery parameters corresponding to capabilities of a radiotherapy treatment machine; and producing treatment plan data for the radiotherapy treatment based on the set of treatment delivery parameters.

Various techniques may be used to produce the set of radiation controls in the continuous computational space (e.g., an infinite-dimensional space). In an example, generating such radiation controls comprises solving an optimization problem for the radiotherapy treatment, and optionally, using optimization variables in the optimization problem such as a set of auxiliary variables related to at least one of the radiation controls, having a relation defined by a linear operator.

The simulation of the radiation dose may include applying a transform in the continuous computational space as a convolution. Such operations are done by convolving a patient-specific dose deposition kernel or fluence deposition matrix and a radiation control corresponding to at least one of irradiation time (e.g., for Gamma knife treatment) or radiation intensity (e.g., for Linac treatment). In this example, each dose deposition kernel or fluence deposition matrix represents a dose rate from a particular sector, a particular collimator, and a particular isocenter, to a particular location in a patient to receive the radiotherapy treatment.

In another example, applying a transform to determine dose includes applying a Fourier transform, such that the simulated dose calculations are represented as a multiplication in Fourier space. In another example, applying the transform includes applying one of a: wavelet, Laplace, Hankel, Mellin, or Hilbert transform.

In a further example, the optimized solution in the continuous computational space is identified from evaluating an optimization problem using a partial differential equation. Also in a further example, the optimized solution in the continuous computational space is identified using variational inference to find an approximate solution. Also in a further example, the optimized solution in the continuous computational space is identified using a probabilistic language of random fields, performing computations using a finite subset of points, and using interpolation to determine properties of the continuous computational space. Also in a further example, the optimized solution in the continuous computational space is identified from applying an optimization using imaging data based on a defined two-dimensional or three-dimensional grid.

In a still further example, the set of treatment delivery parameters generated with such a techniques may be collapsed to a path to perform the radiotherapy treatment, based on a type of the radiotherapy treatment machine. For instance, the collapsing of the set of treatment delivery parameters may be performed using curvelets.

In a still further example, the set of dose calculations produced in the continuous computational space may be based on variables indicating modulation of radiation during the radiotherapy treatment, with the variables defining at least one of: focus position, directionality, irradiation time, flux, fluence, energy, or collimation, for the radiation.

Various forms of radiotherapy and treatment planning may be addressed by these techniques. For instance, data for the radiotherapy treatment may include a definition of one or more volumes, such as data that defines one or more organ at risk areas and one or more target areas. In a further example, the radiotherapy treatment is provided with a Gamma knife, and the set of treatment delivery parameters comprises a set of isocenters used for delivery of the radiotherapy treatment, and the set of treatment delivery parameters may further comprise timing for delivery of the radiotherapy treatment and a sequence for the delivery of the radiotherapy treatment. In another example, the radiotherapy treatment is provided with a Volumetric-modulated arc therapy (VMAT) or Intensity modulated radiation therapy (IMRT) using a Linac (linear accelerator) radiotherapy machine, and the set of treatment delivery parameters comprises a set of arc control points and couch positions. For instance, such treatment plan data may be used to cause or effect delivery of the radiotherapy treatment using a plurality of radiotherapy beams from the radiotherapy treatment machine, based on the calculated treatment plan data for the radiotherapy treatment.

The above overview is intended to provide an overview of subject matter of the present patent application. It is not intended to provide an exclusive or exhaustive explanation of the inventive subject matter. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

FIG. 7 illustrates a flowchart for a method of radiotherapy treatment planning, according to some examples.

DETAILED DESCRIPTION

Figure 1:
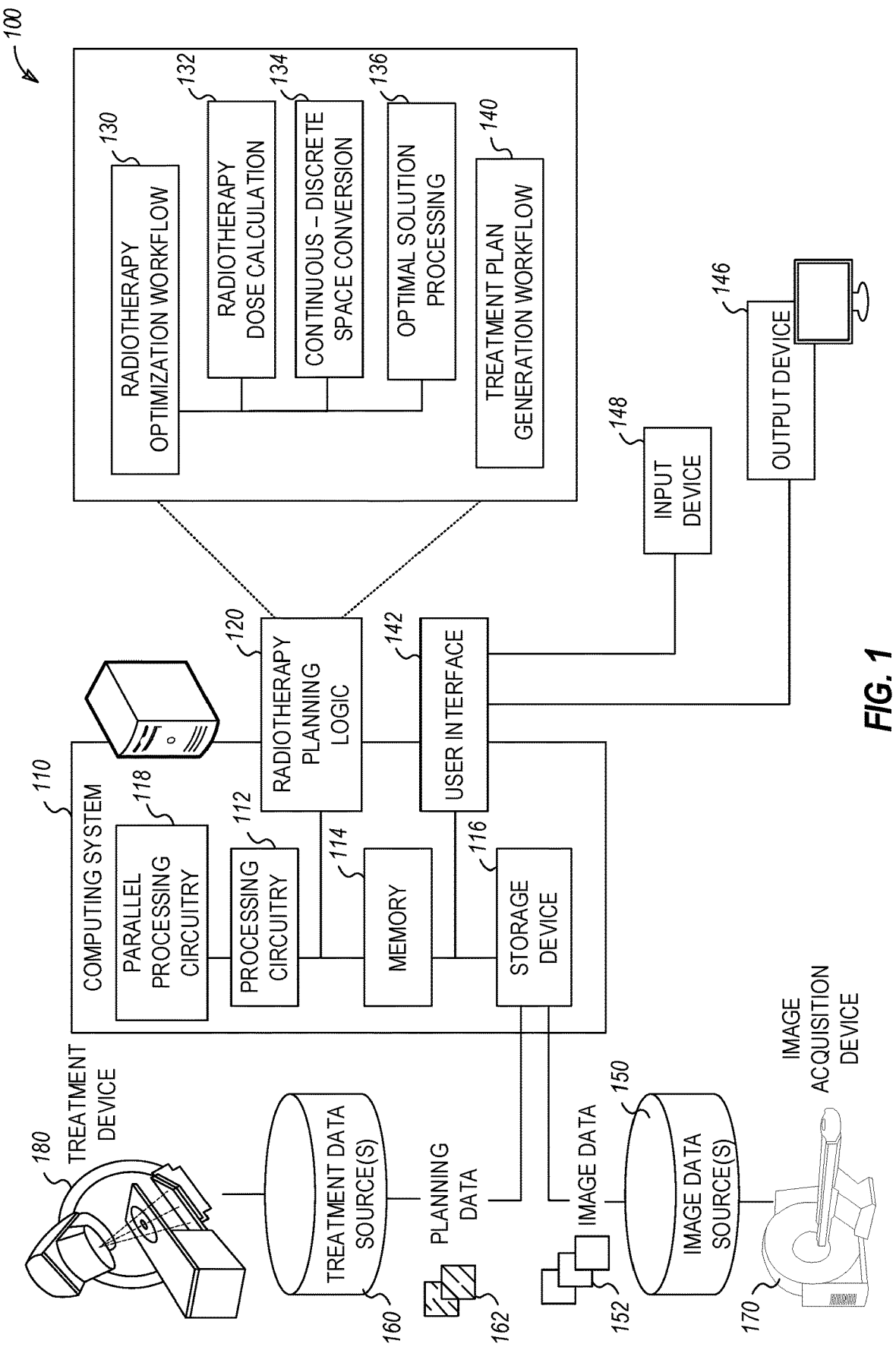
FIG. 1 illustrates a radiotherapy system, according to some examples.

In the following detailed description, reference is made to the accompanying drawings which form a part hereof, and which is shown by way of illustration-specific embodiments in which the present disclosure may be practiced. These embodiments, which are also referred to herein as "examples," are described in sufficient detail to enable those skilled in the art to practice the disclosure, and it is to be understood that the embodiments may be combined, or that other embodiments may be utilized and that structural, logical and electrical changes may be made without departing from the scope of the present disclosure. The following detailed description is, therefore, not to be taken in a limiting sense, and the scope of the present disclosure is defined by the appended claims and their equivalents.

In the examples discussed herein, treatment planning problems are solved by addressing the dose planning stage in a continuum limit, such as by having the degrees of freedom be represented by functions or fields rather than a discrete set of variables. Accordingly, in a Gamma Knife radiotherapy setting, the planning can be approached by considering the optimum irradiation times as a field over $\mathbb{R}^3$, instead of starting with a discrete set of isocenter locations that are identified first and optimized secondly.

The techniques discussed herein may also be applicable to planning for other forms of radiotherapy, which typically involve a similar set of optimization based on a discrete set of variables and parameters. For instance, when evaluating a radiotherapy for VMAT in a continuous space, the result would not be a field over $\mathbb{R}^3$ having isocenters but instead would be a new cylinder shape used to focus the delivery of radiotherapy beams from different beam angles. Likewise, when evaluating a non-coplanar setup, the result would involve analysis of a new conical frustum shape (i.e., a cone with the top cut off) used to focus the delivery of radiotherapy beams. As another example, the patient may be continuously repositioned by translating or rotating the bed.

In an example, the following approaches for treatment planning are implemented by using (i) a computationally tractable method for performing computations with continuous entities, and (ii) a method of converting the continuous entities into treatment plans that can be delivered with a physical radiotherapy treatment machine. Each of these approaches may be customized depending on the type of therapy and constraints to be considered for each therapy.

As used herein, reference to a "continuous computational space" is provided with reference to the computation of some control variable that belongs to an infinite-dimensional space (for example, such a control variable could be a function). Thus, a "continuous computational space" can be considered synonymous to a "infinite-dimensional computational space" and is used interchangeably herein.

Let X and Y be two linear vector spaces and let D be a subset of X. A rule A which associates with every element x∈D an element y∈Y is said to be a mapping (or, equivalently, transformation or operator) from X to Y with domain D. If Y is the real line, A may also be referred to as a (real) functional. The set D where A is defined is called the domain of A. If y=A(x), then y is called the image of x. The image of the entire domain, A(D), is called the range of A. We synonymously refer to an infinite-dimensional vector space as a continuous vector space, or when used for computation, as a continuous computational space. In an example, the domain of A may be infinite-dimensional, i.e. a continuous computational space, and a subset U of the range of A, i.e. U⊆A(D), may be identified with control variables in a radiotherapy treatment plan. Further, an optimization problem may use an objective function comprising a functional J[U] to define a "cost" associated with a given choice of control variables, which is minimized by modifying the mapping A in order to find a desirable choice of control variables.

Figure 8:
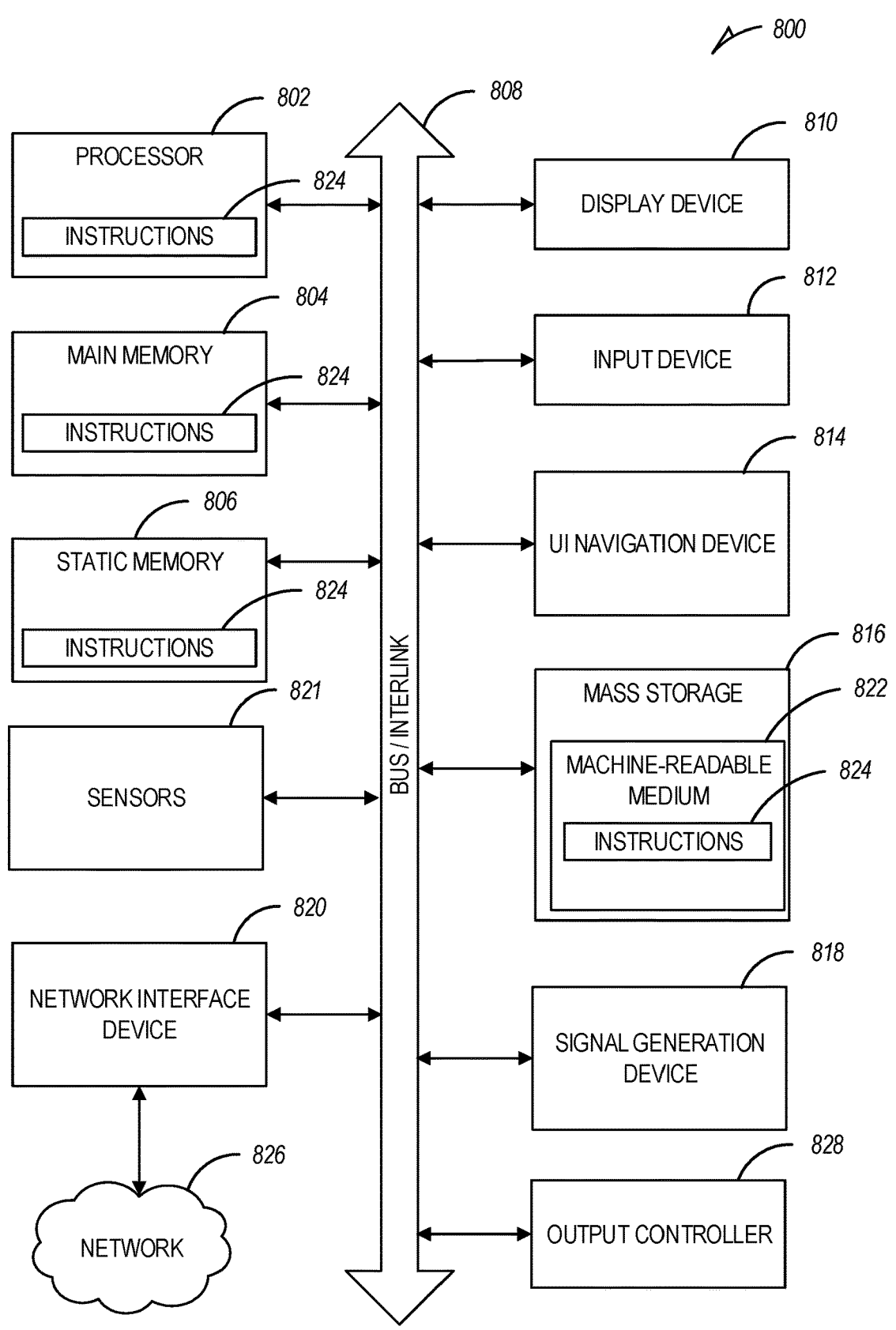
FIG. 8 illustrates an exemplary block diagram of a machine on which one or more of the methods as discussed herein can be implemented.

The following paragraphs provide an overview of example radiotherapy system implementations and treatment use cases (with reference to FIGS. 2A, 2B, 3 and 4), including with the use of computing systems and hardware implementations (with reference to FIGS. 1 and 8). The following then continues with a discussion of example planning and radiation control (e.g., dose calculation) workflows (with reference to FIGS. 5 and 6). Finally, a discussion of radiotherapy treatment planning (with reference to FIG. 7) is provided, which illustrates an end-to-end method of generating a treatment plan with such planning and radiation controls.

FIG. 1 illustrates an exemplary radiotherapy system 100 adapted to perform radiotherapy plan processing operations using one or more of the approaches discussed herein. These radiotherapy plan processing operations are performed to enable the radiotherapy system 100 to provide radiation therapy to a patient based on specific aspects of captured medical imaging data and therapy radiation controls (e.g., dose calculations or radiotherapy machine configuration parameters). Specifically, the following processing operations may be implemented as part of the radiotherapy planning logic 120 for developing a radiotherapy treatment plan. It will be understood, however, that many variations and use cases of the following planning logic 120 and optimization operations may be provided, such as in response to data verification, visualization, and other medical evaluative and diagnostic operations.

The radiotherapy system 100 includes a radiotherapy processing computing system 110 which hosts radiotherapy planning logic 120. The radiotherapy processing computing system 110 may be connected to a network (not shown), and such network may be connected to the Internet. For instance, a network can connect the radiotherapy processing computing system 110 with one or more private and/or public medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device), and a treatment data source 160.

As an example, the radiotherapy processing computing system 110 can be configured to receive a treatment goal of a subject (e.g., from one or more MR images) and generate a radiotherapy treatment plan by executing instructions or data from the radiotherapy planning logic 120, as part of operations to generate treatment plans to be used by the treatment device 180 and/or for output on device 146. In an embodiment, the radiotherapy planning logic 120 solves an optimization problem to generate the radiotherapy treatment plan. The radiotherapy planning logic 120 solves the radiotherapy optimization problem by identifying a new optimal solution to a radiology treatment optimization problem, based on values identified in an continuous computation space.

A generic radiotherapy treatment plan optimization problem can be defined as Equation 1:

$$\underset{x \in X}{\text{minimize}} \ f(x) \qquad \text{(Equation 1)}$$

$$\text{subject to } x \in \Omega$$

where $f: X \rightarrow \mathbb{R}$ is the objective function, $x \in X$ is the decision variables and $\Omega \subseteq X$ is the set of feasible variables. In general, the function $f$ can be nonlinear and the set $\Omega$ non-convex. The optimization problems are typically solved using some form of iterative scheme. For example, in case $f$ is smooth and convex, and $\Omega$ is convex, then the projected gradient scheme could be used to solve equation (1) and reads as follows:

$$x_{n+1} = proj_\Omega(x_n - \eta \nabla f(x_n)) \qquad \text{(Equation 2)}$$

where $proj_\Omega: X \rightarrow X$ is the projection onto $\Omega$, $\eta \in \mathbb{R}$ is a stepsize and $\nabla f: X \rightarrow X$ the gradient. Such optimization problems may be solved using a optimization problem solver (e.g., simplex method, an interior point method, a Newton method, a quasi-Newton method, a Gauss-Newton method, a Levenberg-Marquardt method, a linear least-squares method, a gradient descent method, a projected gradient method, a conjugate gradient method, an augmented Lagrangian method, a Nelder-Mead method, a branch and bound method, a cutting plane method, simulated annealing, and/or sequential quadratic programming) using processing circuitry 112 or parallel processing circuitry 118 or a combination thereof.

The disclosed techniques enhance the efficiency and quality of solving the optimization problem. In particular, allowing the degrees of freedom to be continuous, rather than discrete, leads to an improved quality of the treatment plans, because the expanded feasible set leads to a lower minimum of the treatment plan optimization problem expressed in Equation 1. Moreover, the techniques discussed herein enable evaluation of a larger feasible set than from use of prior continuum techniques.

The radiotherapy processing computing system 110 may include processing circuitry 112, memory 114, a storage device 116, and other hardware and software-operable features such as a user interface 142, a communication interface (not shown), and the like. The storage device 116 may store transitory or non-transitory computer-executable instructions, such as an operating system, radiation therapy treatment plans, training data, software programs (e.g., image processing software, image or anatomical visualization software, artificial intelligence (AI) or ML implementations and algorithms such as provided by deep learning models, ML models, and neural networks (NNs), etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application-specific integrated circuit (ASIC), a field programmable gate array (FPGA), a digital signal processor (DSP), a System on a Chip (SoC), or the like.

As would be appreciated by those skilled in the art, in some examples, the processing circuitry 112 may be a special-purpose processor rather than a general-purpose processor. The processing circuitry 112 may include one or more known processing devices, such as a microprocessor from the Pentium™ Core™, Xeon™, or Itanium® family manufactured by Intel™, the Turion™ Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™ GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one physical (circuitry-based) or software-based processor (for example, a multi-core design or a plurality of processors each having a multi-core design). The processing circuitry 112 can execute sequences of transitory or non-transitory computer program instructions, stored in memory 114, and accessed from the storage device 116, to perform various operations, processes, and methods that will be explained in greater detail below. It should be understood that any component in system 100 may be implemented separately and operate as an independent device and may be coupled to any other component in system 100 to perform the techniques described in this disclosure.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including images, training data, one or more ML model(s) or technique(s) parameters, data, or transitory or non-transitory computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a transitory or non-transitory machine-readable medium on which is stored one or more sets of transitory or non-transitory instructions and data structures (e.g., software) embodying or utilized by any one or more of the methodologies or functions described herein (including, in various examples, the radiotherapy planning logic 120 and the user interface 142). The instructions may also reside, completely or at least partially, within the memory 114 and/or within the processing circuitry 112 during execution thereof by the radiotherapy processing computing system

110, with the memory 114 and the processing circuitry 112 also constituting transitory or non-transitory machine-readable media.

The memory 114 and the storage device 116 may constitute a non-transitory computer-readable medium. For example, the memory 114 and the storage device 116 may store or load transitory or non-transitory instructions for one or more software applications on the computer-readable medium. Software applications stored or loaded with the memory 114 and the storage device 116 may include, for example, an operating system for common computer systems as well as for software-controlled devices. The radiotherapy processing computing system 110 may also operate a variety of software programs comprising software code for implementing the radiotherapy planning logic 120 and the user interface 142. Further, the memory 114 and the storage device 116 may store or load an entire software application, part of a software application, or code or data that is associated with a software application, which is executable by the processing circuitry 112. In a further example, the memory 114 and the storage device 116 may store, load, and manipulate one or more radiation therapy treatment plans, imaging data, segmentation data, treatment visualizations, histograms or measurements, one or more AI model data (e.g., weights and parameters of one or more ML model(s)), training data, labels and mapping data, and the like. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as an IEEE 802.11/Wi-Fi adapter), a telecommunication adapter (e.g., to communicate with 3G, 4G/LTE, and 5G networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, the network may be a LAN or a WAN that may include other systems (including additional image processing computing systems or image-based components associated with medical imaging or radiotherapy operations).

In an example, the radiotherapy processing computing system 110 may obtain image data 152 from the image data source 150 (e.g., MR images) for hosting on the storage device 116 and the memory 114. In yet another example, the software programs may substitute functions of the patient images such as signed distance functions or processed versions of the images that emphasize some aspect of the image information. The radiotherapy processing computing system 110 may obtain or communicate image data 152 from or to image data source 150. In further examples, the treatment data source 160 receives or updates the planning data 162 as a result of a treatment plan generated by the radiotherapy planning logic 120. The image data source 150 may also provide or host the imaging data for use in the radiotherapy planning logic 120.

In an example, computing system 110 may communicate with treatment data source(s) 160, input device 148, and other data sources to generate variables and parameters for a radiotherapy treatment plan optimization problem. Such variables and parameters may be evaluated generated to identify a plurality of optimal solutions (i.e., possible solutions) to the radiotherapy problem. The generated solutions may comprise a pareto-optimal solutions, with a pareto optimal plan referring to a radiotherapy plan where no criterion can be improved without worsening another). The resulting "optimal" solution may be further evaluated and refined before use in a radiotherapy treatment. As will be understood, the pareto-surface of solutions generating with continuous planning parameters will be "below" the pareto-surface generated with discrete planning parameters.

The processing circuitry 112 may be communicatively coupled to the memory 114 and the storage device 116, and the processing circuitry 112 may be configured to execute computer-executable instructions stored thereon from either the memory 114 or the storage device 116. Particularly, radiotherapy planning logic 120 receives an optimization problem that is derived from parameters for radiotherapy treatment. The processing circuitry 112 may utilize software programs or implementations to optimize a plan to deliver a particular radiotherapy dose from a radiotherapy machine, as part of developing an optimized solution to a radiotherapy problem as discussed herein. Further, such software programs or implementations may utilize the radiotherapy planning logic 120 to produce new or updated treatment plan parameters for deployment to the treatment data source 160 and/or presentation on output device 146, using the techniques further discussed herein. The processing circuitry 112 may subsequently then transmit the new or updated treatment plan details via a communication interface and the network to the treatment device 180, where the radiation therapy plan will be used to treat a patient with radiation via the treatment device 180, consistent with results of the radiotherapy planning logic 120 (e.g., according to the processes discussed below).

In an example, the image data 152 used for defining a radiotherapy problem or indicating the anatomical areas of the patient may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, 2D Cone beam CT, 3D CT, 3D CBCT, 4D CT, 4DCBCT), ultrasound images (e.g., 2D ultrasound, 3D ultrasound, 4D ultrasound), Positron Emission Tomography (PET) images, X-ray images, fluoroscopic images, radiotherapy portal images, Single-Photo Emission Computed Tomography (SPECT) images, computer-generated synthetic images (e.g., pseudo-CT images) and the like. Further, the image data 152 may also include or be associated with medical image processing data (for example, training images, ground truth images, contoured images, and dose images). In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise an MRI imaging device, a CT imaging device, a PET imaging device, an ultrasound imaging device, a fluoroscopic device, a SPECT imaging device, an integrated Linear Accelerator and MRI imaging device, CBCT imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., an MRI device combined with a linear accelerator, also referred to as an "MRI-Linac"). Such an MRI-Linac can be used, for example, to determine a location of a target organ or a target tumor in the patient so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, including control points of a radiotherapy treatment device, such as couch position, beam intensity, beam angles, dose-histogram-volume information, the number of radiation beams to be used during therapy, the dose per beam, and the like.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information (e.g., control points) may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may, in some examples, have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device that outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.), treatment plans, a target, localizing a target and/or tracking a target, or any related information to the user. The input device 148 connected to the user interface 142 may be a keyboard, a keypad, a touch screen or any type of device that a user may use to the radiotherapy system 100. Alternatively, the output device 146, the input device 148, and features of the user interface 142 may be integrated into a single device such as a smartphone or tablet computer (e.g., Apple iPad®, Lenovo Thinkpad®, Samsung Galaxy®, etc.).

Furthermore, any and all components of the radiotherapy system may be implemented as a virtual machine (e.g., via VMWare, Hyper-V, and the like virtualization platforms) or independent devices. For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D CBCT or CT or MRI volume. Such 2D slices can be acquired by the image acquisition device 170 in "near real time" while a patient is undergoing radiation therapy treatment (for example, when using the treatment device 180 (with "near real time" meaning acquiring the data in at least milliseconds or less)).

The radiotherapy planning logic 120 in the radiotherapy processing computing system 110 implements a radiotherapy optimization workflow 130 and treatment plan generation workflow 140, The radiotherapy optimization workflow 130 may implement optimization operations for identifying and developing optimal radiology plans in a continuous computational space, before converting to discrete parameters specific to the treatment device 180. In specific examples, the radiotherapy optimization workflow 130 performs radiotherapy dose calculation 132 to obtain and identify one or more solutions in a continuous computational space, continuous-discrete space conversion processing 134 to optionally convert the solution to discrete parameters (e.g., if needed for delivering radiation therapy), and optimal solution processing 136 to identify and output (and, refine) optimal solutions to the optimization problems.

More details of the radiotherapy optimization workflow 130 are provided below with reference to FIGS. 5 and 6. Likewise, more details of the treatment plan generation workflow 140 are provided below with reference to FIGS. 7, which suggest how a treatment plan may be further evaluated, selected, optimized, and deployed for use.

Figure 2A:
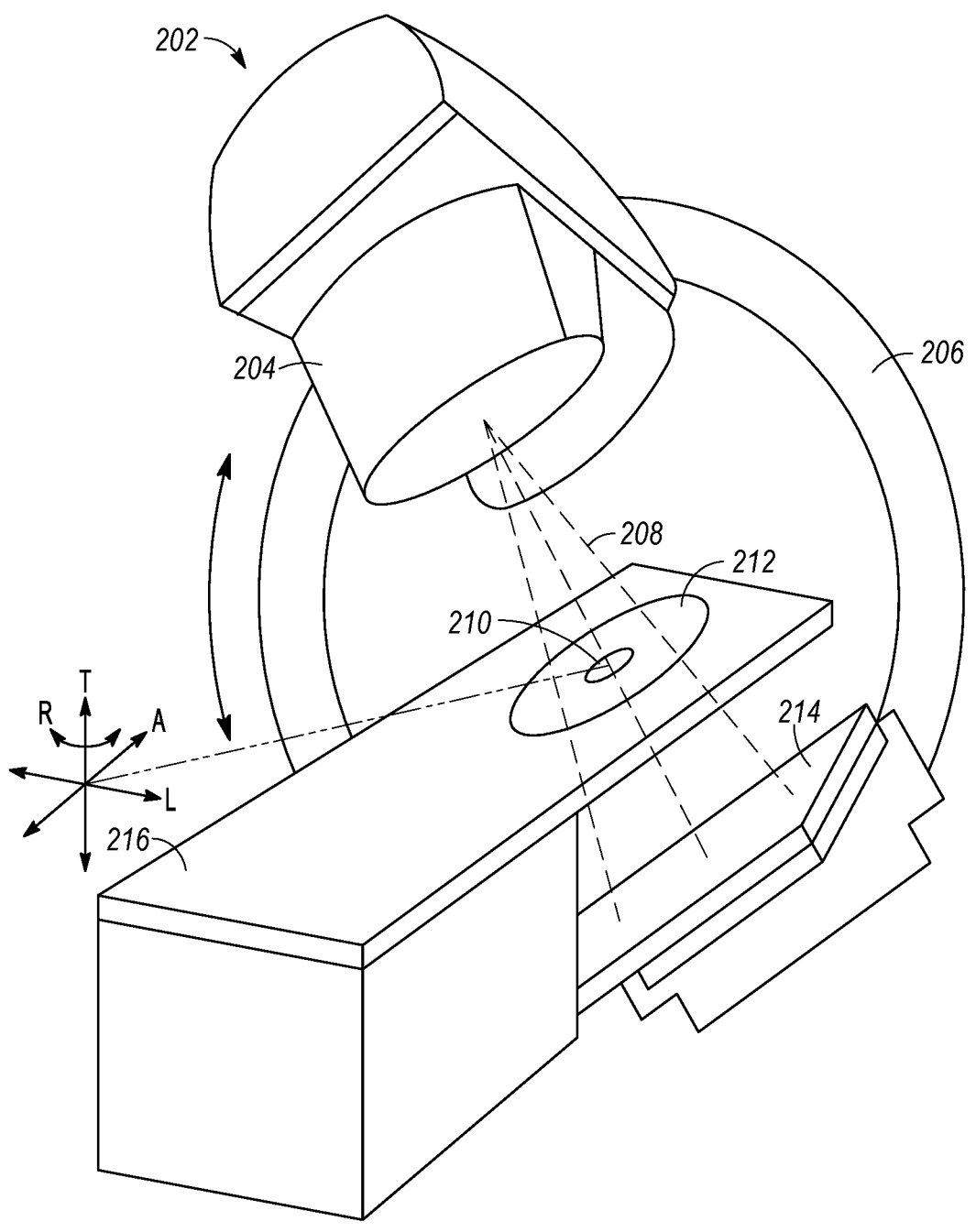
FIG. 2A illustrates a radiation therapy system having radiation therapy output configured to provide a therapy beam, according to some examples.

FIG. 2A illustrates a radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as an MLC. A MLC may be used for shaping, directing, or modulating an intensity of a radiation therapy beam to the specified target locus within the patient. The leaves of the MLC, for instance, can be automatically positioned to define an aperture approximating a tumor cross-section or projection, and cause modulation of the radiation therapy beam. For example, the leaves can include metallic plates, such as comprising tungsten, with a long axis of the plates oriented parallel to a beam direction and having ends oriented orthogonally to the beam direction. Further, a "state" of the MLC can be adjusted adaptively during a course of radiation therapy treatment, such as to establish a therapy beam that better approximates a shape or location of the tumor or other target locus.

Referring back to FIG. 2A, a patient can be positioned in a region 212 and supported by the treatment couch 216 to receive a radiation therapy dose, according to a radiation therapy treatment plan. The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. Both the couch 216 and the gantry 206 are independently moveable from one another in multiple degrees of freedom, which allows the patient to be positioned such that the radiation beam 208 can target the tumor precisely. The MLC may be integrated and included within gantry 206 to deliver the radiation beam 208 of a certain shape.

The coordinate system (including axes A, T, and L) shown in FIG. 2A can have an origin located at an isocenter 210. The isocenter can be defined as a location where the central axis of the radiation beam 208 intersects the origin of a coordinate axis, such as to deliver a prescribed radiation dose to a location on or within a patient. Alternatively, the isocenter 210 can be defined as a location where the central axis of the radiation beam 208 intersects the patient for various rotational positions of the radiation therapy output 204 as positioned by the gantry 206 around the axis A. As discussed herein, the gantry angle corresponds to the position of gantry 206 relative to axis A, although any other axis or combination of axes can be referenced and used to determine the gantry angle.

Gantry 206 may also have an attached imaging detector 214. The imaging detector 214 is preferably located opposite to the radiation source, and in an example, the imaging detector 214 can be located within a field of the radiation beam 208.

The imaging detector 214 can be mounted on the gantry 206 (preferably opposite the radiation therapy output 204), such as to maintain alignment with the radiation beam 208. The imaging detector 214 rotates about the rotational axis as the gantry 206 rotates. In an example, the imaging detector 214 can be a flat panel detector (e.g., a direct detector or a scintillator detector). In this manner, the imaging detector 214 can be used to monitor the radiation beam 208 or the imaging detector 214 can be used for imaging the patient's anatomy, such as portal imaging. The control circuitry of the radiation therapy device 202 may be integrated within the radiotherapy system 100 or remote from it.

In an illustrative example, one or more of the couch 216, the therapy output 204, or the gantry 206 can be automatically positioned, and the therapy output 204 can establish the radiation beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue near the therapy locus can be reduced or avoided.

Figure 2B:
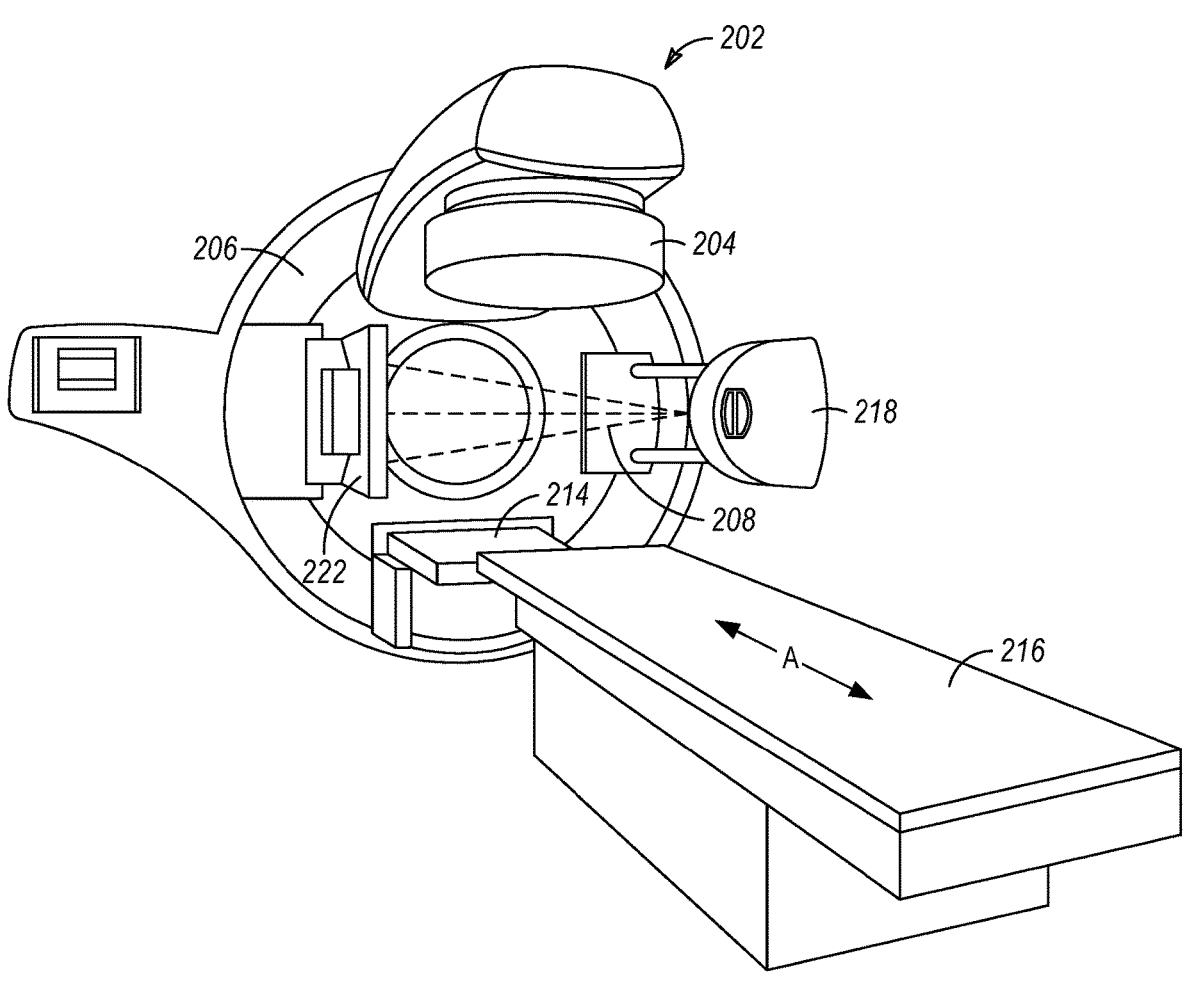
FIG. 2B illustrates a system including a combined radiation therapy system and an imaging system, such as a cone beam computed tomography (CBCT) imaging system, according to some examples.

FIG. 2B illustrates a radiation therapy device 202 that may include a combined LINAC and an imaging system, such as a CT imaging system. The radiation therapy device 202 can include an MLC (not shown). The CT imaging system can include an imaging X-ray source 218, such as providing X-ray energy in a kiloelectron-Volt (keV) energy range. The imaging X-ray source 218 can provide a fan-shaped and/or a conical radiation beam 208 directed to an imaging detector 222, such as a flat panel detector. The radiation therapy device 202 can be similar to the system described in relation to FIG. 2A, such as including a radiation therapy output 204, a gantry 206, a couch 216, and another imaging detector 214 (such as a flat panel detector). The X-ray source 218 can provide a comparatively-lower-energy X-ray diagnostic beam, for imaging.

In the illustrative example of FIG. 2B, the radiation therapy output 204 and the X-ray source 218 can be mounted on the same rotating gantry 206, rotationally separated from each other by 90 degrees. In another example, two or more X-ray sources can be mounted along the circumference of the gantry 206, such as each having its own detector arrangement to provide multiple angles of diagnostic imaging concurrently. Similarly, multiple radiation therapy outputs 204 can be provided.

Figure 3:
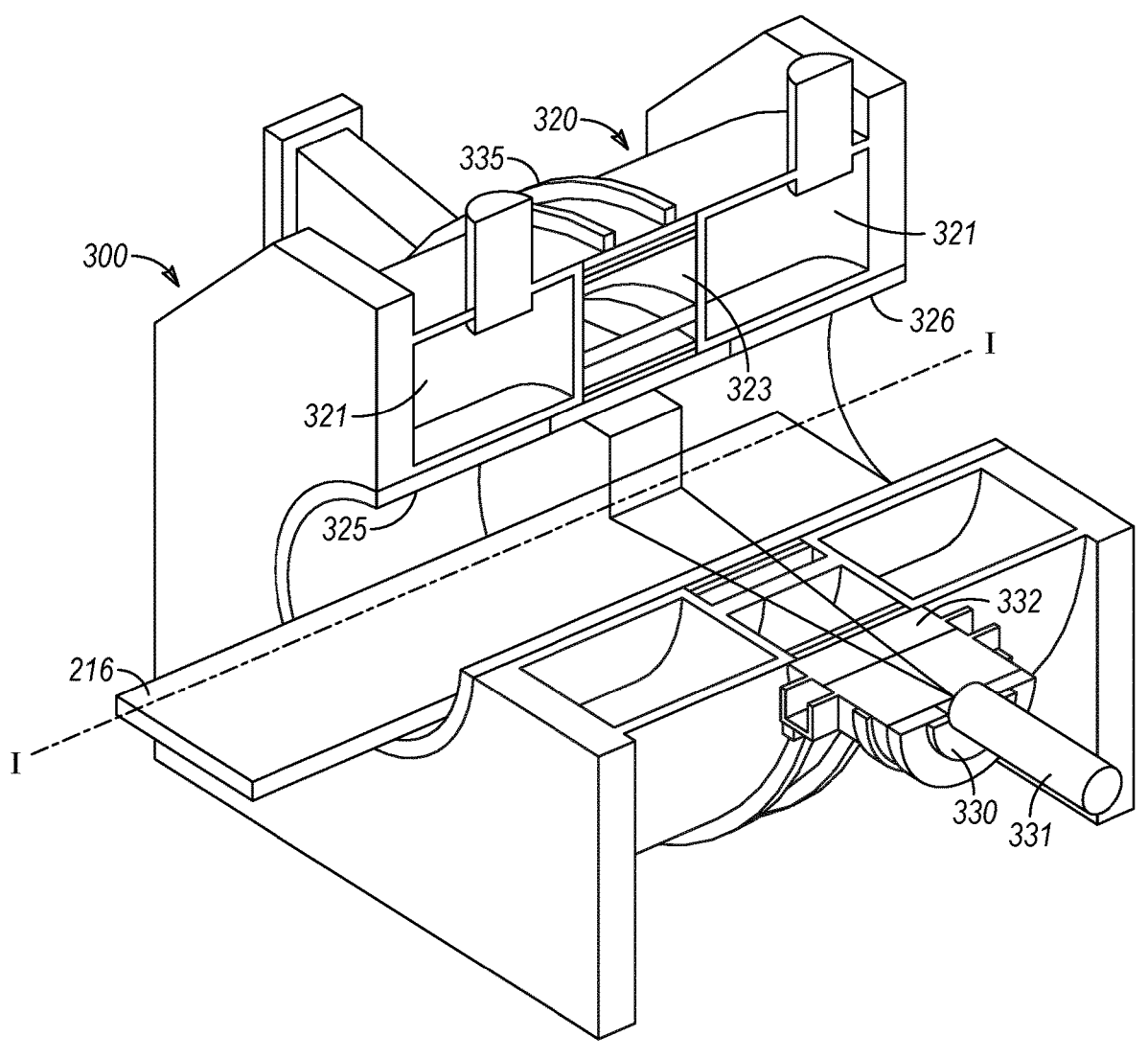
FIG. 3 illustrates a partially cut-away view of a system including a combined radiation therapy system and an imaging system, such as a nuclear magnetic resonance (MR) imaging (MRI) system, according to some examples.

FIG. 3 depicts a radiation therapy system 300 that can include combining a radiation therapy device 202 and an imaging system, such as a magnetic resonance (MR) imaging system (e.g., known in the art as an MR-LINAC) consistent with the disclosed examples. As shown, system 300 may include a couch 216, an image acquisition device 320, and a radiation delivery device 330. System 300 delivers radiation therapy to a patient in accordance with a radiotherapy treatment plan. In some examples, image acquisition device 320 may correspond to image acquisition device 170 in FIG. 1 that may acquire origin images of a first modality (e.g., an MRI image) or destination images of a second modality (e.g., an CT image).

Couch 216 may support a patient (not shown) during a treatment session. In some implementations, couch 216 may move along a horizontal translation axis (labelled "I"), such that couch 216 can move the patient resting on couch 216 into and/or out of system 300. Couch 216 may also rotate around a central vertical axis of rotation, transverse to the translation axis. To allow such movement or rotation, couch 216 may have motors (not shown) enabling the couch 216 to move in various directions and to rotate along various axes. A controller (not shown) may control these movements or rotations in order to properly position the patient according to a treatment plan.

In some examples, image acquisition device 320 may include an MRI machine used to acquire 2D or 3D MRI images of the patient before, during, and/or after a treatment session. Image acquisition device 320 may include a magnet 321 for generating a primary magnetic field for magnetic resonance imaging. The magnetic field lines generated by operation of magnet 321 may run substantially parallel to the central translation axis I. Magnet 321 may include one or more coils with an axis that runs parallel to the translation axis I. In some examples, the one or more coils in magnet 321 may be spaced such that a central window 323 of magnet 321 is free of coils. In other examples, the coils in magnet 321 may be thin enough or of a reduced density such that they are substantially transparent to radiation of the wavelength generated by radiotherapy device 330. Image acquisition device 320 may also include one or more shielding coils, which may generate a magnetic field outside magnet 321 of approximately equal magnitude and opposite polarity in order to cancel or reduce any magnetic field outside of magnet 321. As described below, radiation source 331 of radiation delivery device 330 may be positioned in the region where the magnetic field is cancelled, at least to a first order, or reduced.

Image acquisition device 320 may also include two gradient coils 325 and 326, which may generate a gradient magnetic field that is superposed on the primary magnetic field. Coils 325 and 326 may generate a gradient in the resultant magnetic field that allows spatial encoding of the protons so that their position can be determined. Gradient coils 325 and 326 may be positioned around a common central axis with the magnet 321 and may be displaced along that central axis. The displacement may create a gap, or window, between coils 325 and 326. In examples where magnet 321 can also include a central window 323 between coils, the two windows may be aligned with each other.

In some examples, image acquisition device 320 may be an imaging device other than an MRI, such as an X-ray, a CT, a CBCT, a spiral CT, a PET, a SPECT, an optical tomography, a fluorescence imaging, ultrasound imaging, radiotherapy portal imaging device, or the like. As would be recognized by one of ordinary skill in the art, the above description of image acquisition device 320 concerns certain examples and is not intended to be limiting.

Radiation delivery device 330 may include the radiation source 331, such as an X-ray source or a LINAC, and an MLC 332. Radiation delivery device 330 may be mounted on a chassis 335. One or more chassis motors (not shown) may rotate the chassis 335 around the couch 216 when the couch 216 is inserted into the treatment area. In an example, the chassis 335 may be continuously rotatable around the couch 216, when the couch 216 is inserted into the treatment area. Chassis 335 may also have an attached radiation detector (not shown), preferably located opposite to radiation source 331 and with the rotational axis of the chassis 335 positioned between the radiation source 331 and the detector. Further, the device 330 may include control circuitry (not shown) used to control, for example, one or more of the couch 216, image acquisition device 320, and radiotherapy device 330. The control circuitry of the radiation delivery device 330 may be integrated within the system 300 or remote from it.

During a radiotherapy treatment session, a patient may be positioned on couch 216. System 300 may then move couch 216 into the treatment area defined by the magnet 321, coils 325, 326, and chassis 335. Control circuitry may then control radiation source 331, MLC 332, and the chassis motor(s) to deliver radiation to the patient through the window between coils 325 and 326 according to a radiotherapy treatment plan.

FIG. 2A, FIG. 2B, and FIG. 3 generally illustrate examples of a radiation therapy device configured to provide radiotherapy treatment to a patient, using a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient.

Figure 4:
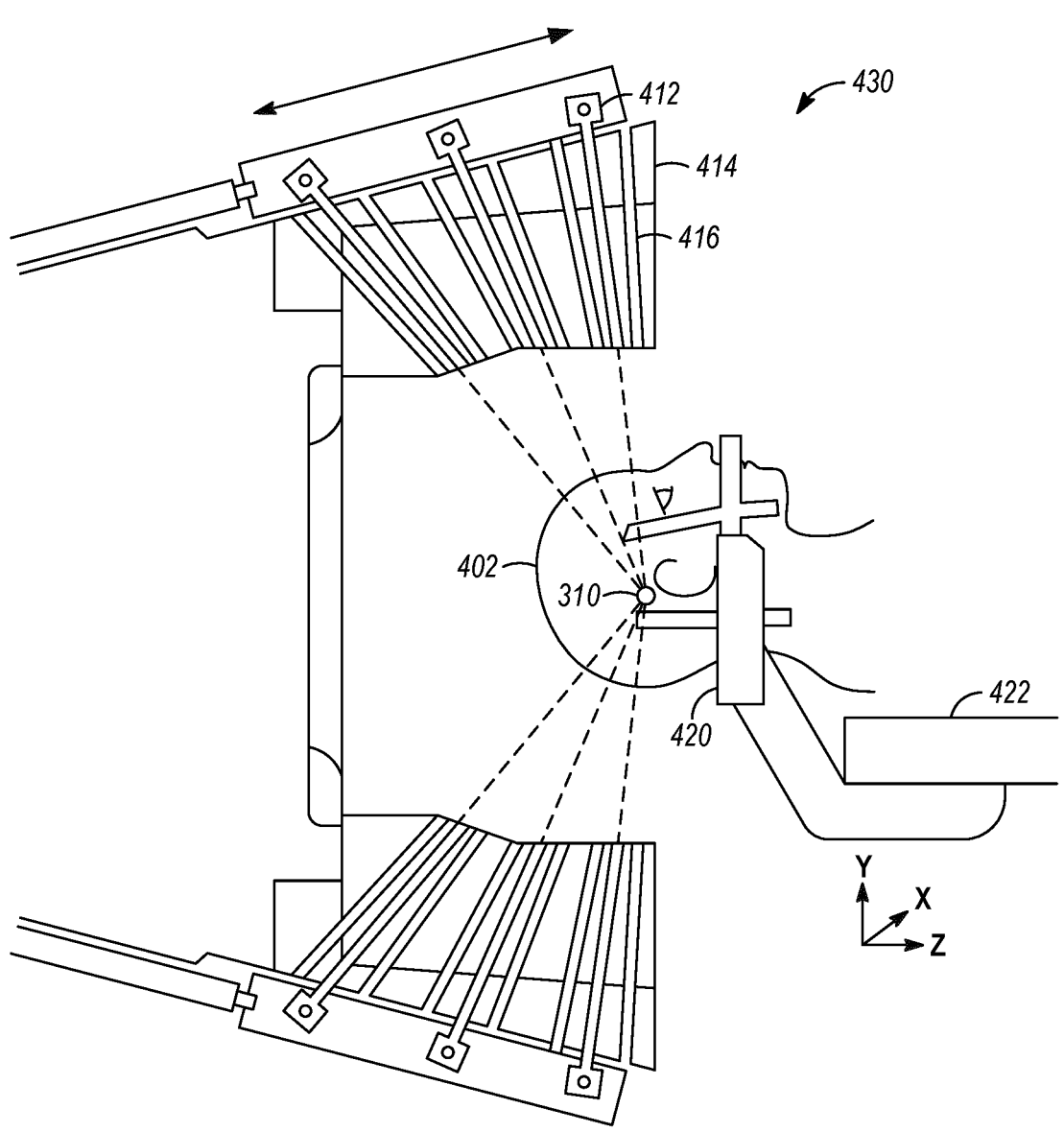
FIG. 4 illustrates an example of a Leksell Gamma Knife radiotherapy device, according to some examples.

FIG. 4 illustrates a contrasting example of a Leksell Gamma Knife radiotherapy device 430, which provides such radiotherapy treatment by means of gamma radiation. As a brief overview of a Gamma Knife device, radiation is emitted from a large number of fixed radioactive sources and is focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all or some radiation sources intersect or converge, causing the radiation to reach tissue-destructive levels. The point of convergence is hereinafter referred to as the "isocenter" but may also be referred to as a "focus point".

As shown in FIG. 4, in a radiotherapy treatment session of a Gamma Knife device, a patient 402 may wear a coordinate frame 420 to keep stable the patient's body part (e.g., the head) undergoing surgery or radiotherapy. Coordinate frame 420 and a patient positioning system 422 may establish a spatial coordinate system, which may be used while imaging a patient or during radiation surgery. Radiotherapy device 430 may include a protective housing 414 to enclose a plurality of radiation sources 412. Radiation sources 412 may generate a plurality of radiation beams (e.g., beamlets) through beam channels 416. The plurality of radiation beams may be configured to focus on an isocenter 310 from different directions. While each individual radiation beam may have a relatively low intensity, isocenter 310 may receive a relatively high level of radiation when multiple doses from different radiation beams accumulate at isocenter 310. In certain examples, isocenter 310 may correspond to a target under surgery or treatment, such as a tumor.

Other types of radiotherapy devices (not illustrated) use protons and/or ions to deliver the radiotherapy treatment. With any of the types of radiotherapy devices, the direction and shape of the radiation beam must be accurately controlled to ensure that the tumor receives the prescribed radiation dose, and the radiation from the beam should minimize damage to the surrounding healthy tissue, especially the organ(s) at risk (OARs). Treatment planning can be used to control radiation beam parameters, and a radiotherapy device effectuates a treatment by delivering a spatially varying dose distribution to the patient.

Treatment plan optimization for radiation therapy, including for gamma knife radiosurgery, aims at maximizing the dose delivered to the target volume within the patient (e.g. in treatment of tumors) at the same time as the dose delivered to adjacent normal tissues is minimized. In treatment plan optimization, the delivered radiation dose is limited by two competing factors: the first one is delivering a high dose to the target volume and the second one is delivering low dose to the surrounding normal tissues.

The treatment plan optimization is a process including optimizing the number of shots being used, the sector-collimator combinations, the shot times, and the position of the shot (i.e. isocenter). Clearly, the irregularity and size of a target volume greatly influence the number of shots needed and the size of the shots being used to optimize the treatment. Thus, for gamma knife radiotherapy, the selected isocenter locations and their corresponding shots for a given case constitutes a treatment plan. An isocenter is defined as a focal point of all beams, and a shot at the given isocenter is defined as the set of sector-collimator combinations with their dwell times used for that isocenter. Selected isocenter locations and their corresponding shots for a given case constitutes a treatment plan.

Treatment plans are often designed or initiated manually by clinical experts. Such manual designs are often challenging and time consuming as the planners are faced with many interdependent decisions. Many studies aim to select isocenter locations based on the geometry of the tumor and nearby organ(s) at risk (OAR(s)), followed by optimization of treatment from such isocenter locations. The present approaches first attempt to identify starting points for such treatment plan designs, followed by conversion and adaptation of such treatment plan designs to the discrete characteristics of a radiotherapy treatment device.

As set forth herein, generating a set of radiation controls for radiotherapy treatment may involve solving an optimization problem for the radiotherapy treatment. The optimization problem may include a set of auxiliary variables (e.g., dose) related to at least one of the radiation controls, having a relation defined by a linear operator. Here, the objective function may be decomposed into two sets of functions (e.g., treatment complexity loss+dose-based loss), one of which is independent of the auxiliary variables FIG. 5 provides a high-level view of radiotherapy treatment planning using continuum-based dose planning. Specifically, this workflow uses one or more computationally tractable methods for generating an optimized solution in the continuous (infinite-dimensional) computational space from among a plurality of potential solutions. This solution provides a starting design for further selection, modification, refinement, and optimization of a radiotherapy treatment plan. For instance, a resulting simulation of a radiation dose distribution may take an infinite-dimensional input and simulate the resulting dose in a (dose) grid roughly aligned with the treatment planning images. (Such an example of a dose grid often has a different resolution from the imaging data).

Figure 5:
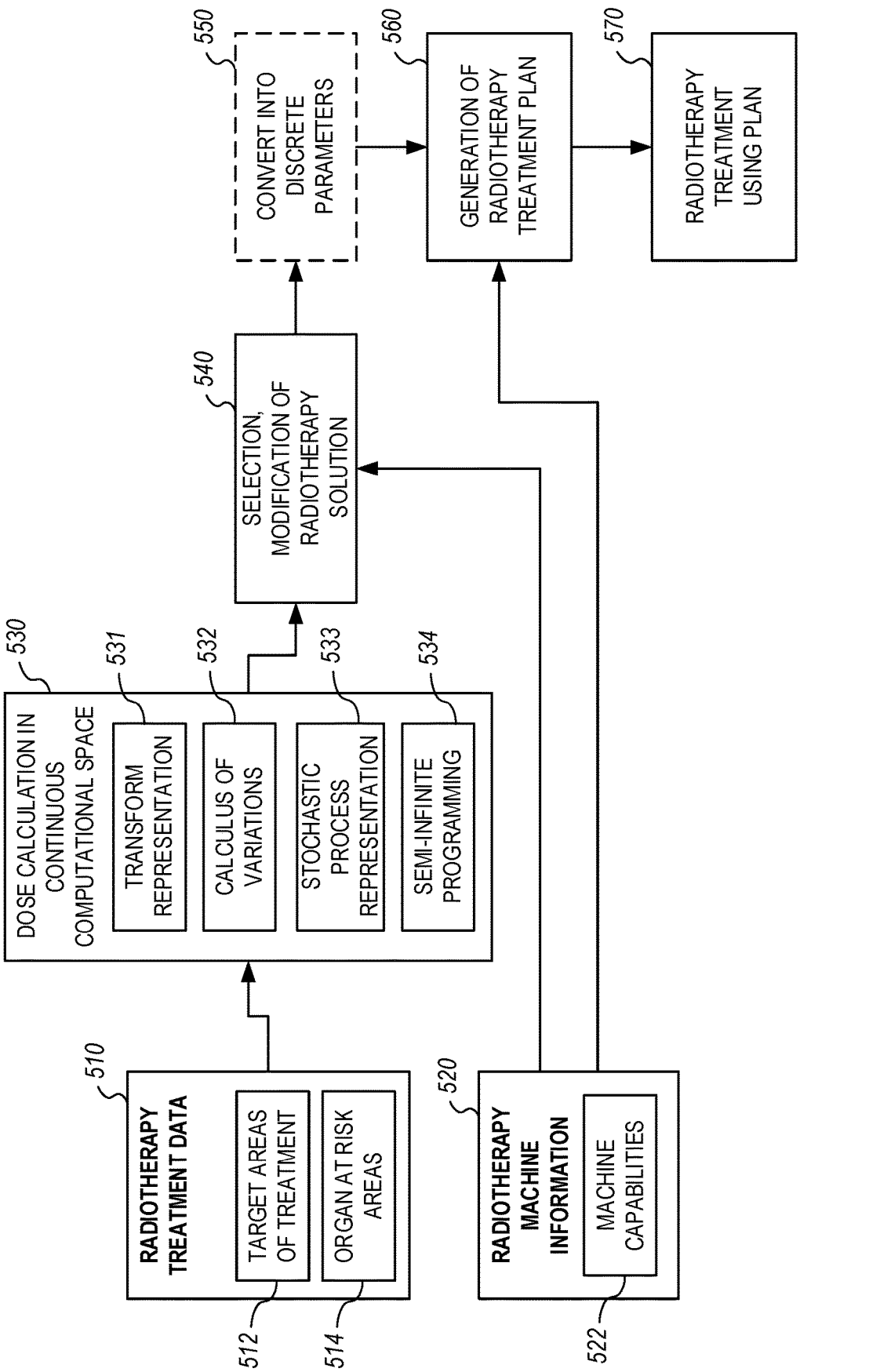
FIG. 5 illustrates a radiotherapy treatment planning workflow using continuum-based dose planning, according to some examples.

The operations in FIG. 5, in more detail, illustrate how radiotherapy treatment data 510, defining treatment objectives for a human subject, are provided within information such as target areas of treatment 512 and organ at risk areas 514. Other information relevant to the radiotherapy problem may include radiotherapy machine information 520 such as machine capabilities 522, which are used later in the operations of FIG. 5.

The treatment data 510 is analyzed by one or more dose calculation methods in operation 530. The methods of operation 530 may include:

Transform representation 531. In this example, a transform is applied to turn a symmetry of (parts of) the optimization problem into a computational advantage. For instance, dose calculations in radiotherapy can often be approximated reasonably accurately using convolutions. In particular, a constraint matrix in a treatment optimizer may contain dose deposition kernels or, specifically, dose rate kernels, i.e. the dose rate from a particular sector, collimator and isocenter to an arbitrary voxel in one of the structures (target, inner and low dose ring and organs at risk). A good approximation is that the dose rate kernel is shift invariant, thus it can be expressed as:

$$\Phi(r, \xi) \approx \Phi(r - \xi) \qquad \text{(Equation 3)}$$

where r is the voxel position and $\xi$ is the isocenter location. Dose can thus conveniently be written as a convolution between the dose rate kernel and the irradiation time $t(\xi)$ at $\xi$.

Expressing the dose calculation as a convolution allows expression as a multiplication in Fourier space. Thus, instead of storing the entire dose rate kernel, it is sufficient to pre-calculate $\hat{\Phi}(k)$ the Fourier transform of the dose rate kernel. In certain cases, the entire treatment plan may even be performed in transform space.

In addition to the Fourier transform highlighted above, there other integral transforms may be used, such as wavelets, Laplace, Hankel, Mellin and Hilbert, among others.

Calculus of variations 532. Calculus of variations is a mathematical framework for optimization over functions. In particular, the Euler-Lagrange equation is a partial differential equation (PDE) that provides necessary conditions for a function to be optimal. The Euler-Lagrange equation can be used to convert a continuum treatment planning problem into a partial differential equation that may be solved using standard approaches. In the present scenarios, an approximate solution to the continuum treatment planning problem may be identified as an extrema of a functional derivative. (This is equivalent to the functional derivate being equal to zero, and enforcing that condition gives the Euler-Lagrange equation. Solving the Euler-Lagrange equation is thus a method for finding an extrema). Thus, in an example, an approximation of the solution to the optimization problem is found by assuming a factorization of the solution and using mean-field variational inference to find an extremum of a functional, such that the extrema factorizes according to the assumed factorization.

Variational inference is a particular set of methods that uses calculus of variations to approximate a complicated probability distribution with a simpler one. It is widely used in machine learning but also has close ties to the mean-field theory that is used in theoretical physics. In the present scenarios, variational inference can be used to efficiently find an approximate solution to the continuum treatment planning problem.

Stochastic process representation 533. The interrelation between different points in the field can be mathematically captured using the probabilistic language of stochastic processes (i.e., random fields). Based on such an assumption, it can be possible to perform computations involving only a finite subset of points, which then by means of (numerical or analytical) interpolation determine the properties of the continuous field.

Semi-Infinite Programming 534. Semi-infinite programming refers to optimization problems with an infinite number of variables and an infinite number of constraints, or an infinite number of variables and an infinite number of constraints (because of duality one may often choose which case is most convenient to work with). In the radiotherapy planning setting, the optimization problem is usually defined based on imaging data given on a finite 2D or 3D grid. For this reason, the continuum version of the treatment planning problems often belongs to the class of semi-infinite programming problems, and may be addressed using the toolbox developed in this branch of optimization theory.

A suitable dose calculation to be delivered with radiotherapy problem is then developed in the continuous computational space (e.g., using continuous degrees of freedom) with the depicted radiotherapy calculation operation 530. The calculation operation 530 produces a plurality of potential radiotherapy solutions, which may include pareto-optimal solutions. One or more of these solutions may be selected and modified with operation 540, and used for generation of a particular radiotherapy treatment plan with operation 560. Optionally, one or more aspects of the radiotherapy solution may be converted or modified at operation 550, to conform to discrete treatment parameters. The generation of the radiotherapy treatment plan with operation 560 (and, related selection or modification of the radiotherapy solution) may be dependent on machine capabilities 522. Finally, radiotherapy treatment may be delivered with operation 570 using the generated treatment plan.

Figure 6:
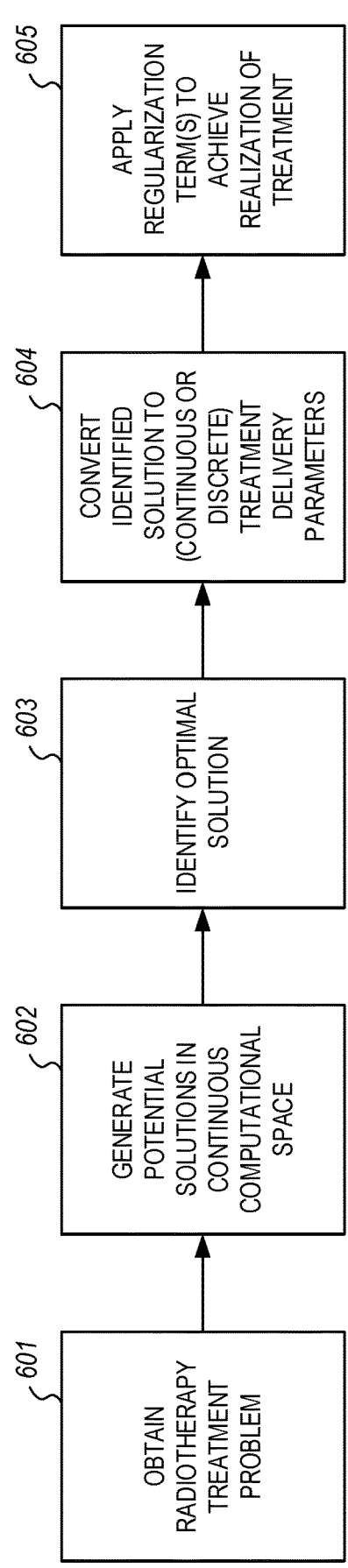
FIG. 6 illustrates additional details on continuum-based dose planning, according to some examples.

FIG. 6 provides additional details on continuum-based dose planning, demonstrating operations performed in a continuous computational space (and, as applicable, operations performed in a discrete computational space). In an example, the sequence of operations includes:

Operation 601: Obtain data which defines the radiotherapy treatment problem, used for radiotherapy treatment of a human subject.

Operation 602: Generate radiotherapy operations in the continuous computational space which provide potential solutions.

Operation 603: Identify an optimal solution (i.e., an "optimized solution") as a starting point for radiotherapy treatment. In the Gamma Knife example, the optimized solution includes time as a function of isocenter position, which is a continuous 3D-vector field.

Operation 604: Convert the identified optimal solution to a set of treatment delivery parameters. In an example, converting the identified optimal solution to the set of treatment delivery parameters is based on minimizing a degradation of plan quality according to a clinically relevant objective (e.g., a clinical metric).

Operation 605: Apply regularization terms, or other methods, to achieve realization of the treatment using continuous or discrete parameters of the radiotherapy treatment. In the Gamma Knife treatment example, a Gamma Knife can position isocenters to an extreme precision and thus can utilize continuous parameters. However, regularization, as discussed in the following paragraph, may be used to reduce the 3D-vector field into a 1D-vector field (i.e. path), to achieve a realizable plan.

It will be understood that various optimizations may be applied to achieve realization of the plan. Solving the optimization problem with irradiation times as a field most likely will lead to a solution that is dense, i.e. non-zero in most of the points in the target. Such solution, although theoretically interesting, will be very difficult to deliver in practice. Introducing some sort of a regularization term in the optimization, forcing the times to "collapse" to a path (i.e., in a field over $\mathbb{R}^1$), would lead to a more tractable problem to solve and also possible to deliver, such as if the treatment couch or the sources can move continuously. As suggested above, one way of achieving the collapse to a path would be to formulate the optimization problem using curvelets rather than in a coordinate basis.

In various examples, the computational steps and the realization steps may be performed in tandem; however, there are advantages to decoupling them. In particular, only the realization step depends on the specifics of the treatment machine, which means that the computational step could, in principle, be shared across a full range of radiotherapy treatment systems.

FIG. 7 illustrates a flowchart 700 of a method of radiotherapy treatment planning based on the techniques discussed above. For instance, the following features of flowchart 700 may be integrated or adapted with the workflow operations discussed with reference to FIG. 5, and dose planning operations discussed with reference to FIG. 6.

Operation 710 begins with operations to obtain data for a radiotherapy treatment of a human subject, with the data defining one or more volumes or other areas designated to receive the radiotherapy treatment from a radiotherapy treatment machine. This data may provide a definition of one or more target areas and one or more organ at risk areas, within the anatomical areas of the human subject to receive (or not to receive) the radiotherapy treatment from the radiotherapy treatment machine.

Operation 720 proceeds with operations to generate dose calculations in a continuous computational space (e.g., in a continuous manner rather than in a discrete manner). The operations to generate the dose calculations may include the sub-steps depicted in operations 730 and 740. Operation 730 proceeds to produce dose calculations of the radiology treatment from a computationally tractable method, and operation 740 proceeds to identify a particular set of dose calculations as an optimized solution.

One example of a computationally tractable method is detailed in operation 730 as applying a transform to produce the set of dose calculations. In this example, the set of dose calculations are approximated in the continuous computational space using convolutions, and a respective dose is represented by a convolution between a dose rate kernel and an irradiation time. Further, each dose rate kernel may represent a dose rate from a particular sector, a particular collimator, and a particular isocenter, to a particular voxel in the one or more volumes to receive the radiotherapy treatment. In a specific example, applying the transform comprises applying a Fourier transform, and the set of dose calculations are represented as a multiplication in Fourier space, as discussed above. In another example, applying the transform comprises applying one of a: wavelet, Laplace, Hankel, Mellin, or Hilbert transform.

Another example of a computationally tractable method is detailed in operation 730 as applying a calculus of variations. This may include applying a partial differential equation, as discussed above.

Another example of a computationally tractable method is detailed in operation 730 as applying a variational inference.

Applying a variational inference may be used to find an approximate solution, as discussed above.

Another example of a computationally tractable method is detailed in operation 730 as applying a stochastic process representation. Applying a Stochastic process representation may include using a probabilistic language of random fields, performing computations using a finite subset of points, and using interpolation to determine properties of the continuous computational space, as discussed above.

Another example of a computationally tractable method is detailed in operation 730 as applying a semi-infinite programming technique. Applying a semi-infinite programming technique may include applying an optimization using imaging data based on a defined two-dimensional or three-dimensional grid.

At operation 750, the set of dose calculations may be optionally converted to a set of treatment delivery parameters which correspond to capabilities of the radiotherapy treatment machine. The dose calculations may be converted from a set of variables which indicate modulation of radiation during the radiotherapy treatment, the variables defining at least one of: focus position, directionality, flux, fluence, energy, or collimation, for the radiation to be delivered. The treatment delivery parameters may be continuous (isocenter position, position, fluence, dose rate, couch speed, etc.) or discrete in nature. In a specific example, depicted at optional operation 760, the high dimensional solution field is collapsed to a path to perform the radiotherapy treatment, based on a type of the radiotherapy treatment machine. For instance, the collapsing of treatment delivery parameters may be performed using curvelets.

At operation 770, the parameters are used to generate a treatment plan for delivery of the radiotherapy. As noted above, the treatment plan may be established with continuous or discrete parameters. Such parameters may be further refined and optimized, using further techniques not discussed herein. For example, with gamma knife treatment, the set of treatment delivery parameters may comprise a set of isocenters used for delivery of the radiotherapy treatment. Also for example, with Volumetric-modulated arc therapy (VMAT) or Intensity modulated radiation therapy (EIRT), the set of treatment delivery parameters may comprise a set of arc control points and couch positions. Such delivery parameters may be continuous or discrete in nature. For example, instead of introducing discrete isocenters, a treatment machine couch may move continuously along a path (which is the solution to the optimization step) during beam-on phase. For VMAT, a specific definition of arc control points may not necessary, as the delivery can be continuous.

FIG. 8 illustrates a block diagram of an example of a machine 800 on which one or more of the methods as discussed herein can be implemented. In one or more examples, one or more items of the radiotherapy processing computing system 110 can be implemented by the machine 800. In alternative examples, the machine 800 operates as a standalone device or may be connected (e.g., networked) to other machines. In one or more examples, the radiotherapy processing computing system 110 can include one or more of the items of the machine 800. In a networked deployment, the machine 800 may operate in the capacity of a server or a client machine in server-client network environment, or as a peer machine in a peer-to-peer (or distributed) network environment. The machine may be a personal computer (PC), server, a tablet, smartphone, a web appliance, edge computing device, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example machine 800 includes processing circuitry or processor 802 (e.g., a CPU, a graphics processing unit (GPU), an ASIC, circuitry, such as one or more transistors, resistors, capacitors, inductors, diodes, logic gates, multiplexers, buffers, modulators, demodulators, radios (e.g., transmit or receive radios or transceivers), sensors 821 (e.g., a transducer that converts one form of energy (e.g., light, heat, electrical, mechanical, or other energy) to another form of energy), or the like, or a combination thereof), a main memory 804 and a static memory 806, which communicate with each other via a bus 808. The machine 800 (e.g., computer system) may further include a video display device 810 (e.g., a liquid crystal display (LCD) or a cathode ray tube (CRT)). The machine 800 also includes an alphanumeric input device 812 (e.g., a keyboard), a user interface (UI) navigation device 814 (e.g., a mouse), a disk drive or mass storage unit 816, a signal generation device 818 (e.g., a speaker), and a network interface device 820.

The disk drive unit 816 includes a machine-readable medium 822 on which is stored one or more sets of instructions and data structures (e.g., software) 824 embodying or utilized by any one or more of the methodologies or functions described herein. The instructions 824 may also reside, completely or at least partially, within the main memory 804 and/or within the processor 802 during execution thereof by the machine 800, the main memory 804 and the processor 802 also constituting machine-readable media.

The machine 800 as illustrated includes an output controller 828. The output controller 828 manages data flow to/from the machine 800. The output controller 828 is sometimes called a device controller, with software that directly interacts with the output controller 828 being called a device driver.

While the machine-readable medium 822 is shown in an example to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present disclosure, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), EEPROM, and flash memory devices; magnetic disks such as internal hard disks and removable disks; magneto-optical disks; and CD-ROM and DVD-ROM disks.

The instructions 824 may further be transmitted or received over a communications network 826 using a transmission medium. The instructions 824 may be transmitted using the network interface device 820 and any one of a number of well-known transfer protocols (e.g., HTTP). Examples of communication networks include a LAN, a WAN, the Internet, mobile telephone networks, Plain Old Telephone (POTS) networks, and wireless data networks (e.g., Wi-Fi and 4G/5G data networks). The term "transmission medium" shall be taken to include any intangible medium that is capable of storing, encoding or carrying instructions for execution by the machine, and includes digital or analog communications signals or other intangible media to facilitate communication of such software.

As used herein, "communicatively coupled between" means that the entities on either of the coupling must communicate through an item therebetween and that those entities cannot communicate with each other without communicating through the item.

ADDITIONAL NOTES

The above detailed description includes references to the accompanying drawings, which form a part of the detailed description. The drawings show, by way of illustration but not by way of limitation, specific embodiments in which the disclosure can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the disclosure or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," and so forth, are used merely as labels, and are not intended to impose numerical requirements on their objects.

Embodiments of the disclosure may be implemented with computer-executable instructions. The computer-executable instructions (e.g., software code) may be organized into one or more computer-executable components or modules. Aspects of the disclosure may be implemented with any number and organization of such components or modules. For example, aspects of the disclosure are not limited to the specific computer-executable instructions or the specific components or modules illustrated in the figures and described herein. Other embodiments of the disclosure may include different computer-executable instructions or components having more or less functionality than illustrated and described herein.

Method examples (e.g., operations and functions) described herein can be machine or computer-implemented at least in part (e.g., implemented as software code or instructions). Some examples can include a computer-readable medium or machine-readable medium encoded with instructions operable to configure an electronic device to perform methods as described in the above examples. An implementation of such methods can include software code, such as microcode, assembly language code, a higher-level language code, or the like (e.g., "source code"). Such software code can include computer-readable instructions for performing various methods (e.g., "object" or "executable code"). The software code may form portions of computer program products. Software implementations of the embodiments described herein may be provided via an article of manufacture with the code or instructions stored thereon, or via a method of operating a communication interface to send data via a communication interface (e.g., wirelessly, over the internet, via satellite communications, and the like).

Further, the software code may be tangibly stored on one or more volatile or non-volatile computer-readable storage media during execution or at other times. These computer-readable storage media may include any mechanism that stores information in a form accessible by a machine (e.g., computing device, electronic system, and the like), such as, but are not limited to, floppy disks, hard disks, removable magnetic disks, any form of magnetic disk storage media, CD-ROMS, magnetic-optical disks, removable optical disks (e.g., compact disks and digital video disks), flash memory devices, magnetic cassettes, memory cards or sticks (e.g., secure digital cards), RAMs (e.g., CMOS RAM and the like), recordable/non-recordable media (e.g., read only memories (ROMs)), EPROMS, EEPROMS, or any type of media suitable for storing electronic instructions, and the like. Such computer-readable storage medium is coupled to a computer system bus to be accessible by the processor and other parts of the OIS.

In an embodiment, the computer-readable storage medium may have encoded a data structure for treatment planning, wherein the treatment plan may be adaptive. The data structure for the computer-readable storage medium may be at least one of a Digital Imaging and Communications in Medicine (DICOM) format, an extended DICOM format, an XML format, and the like. DICOM is an international communications standard that defines the format used to transfer medical image-related data between various types of medical equipment. DICOM RT refers to the communication standards that are specific to radiation therapy.

In various embodiments of the disclosure, the method of creating a component or module can be implemented in software, hardware, or a combination thereof. The methods provided by various embodiments of the present disclosure, for example, can be implemented in software by using standard programming languages such as, for example, C, C++, C#, Java, Python, CUDA programming, and the like; and combinations thereof. As used herein, the terms "software" and "firmware" are interchangeable, and include any computer program stored in memory for execution by a computer.

A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general purpose computer selectively activated or reconfigured by a computer program stored in the computer. The order of execution or performance of the operations in embodiments of the disclosure illustrated and described herein is not essential, unless otherwise specified. That is, the operations may be performed in any order, unless otherwise specified, and embodiments of the disclosure may include additional or fewer operations than those disclosed herein. For example, it is contemplated that executing or performing a particular operation before, contemporaneously with, or after another operation is within the scope of aspects of the disclosure.

In view of the above, it will be seen that the several objects of the disclosure are achieved and other advantageous results attained. Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the disclosure without departing from its scope. While the dimensions, types of materials and coatings described herein are intended to define the parameters of the disclosure, they are by no means limiting and are exemplary embodiments. Many other embodiments will be apparent to those of skill in the art upon reviewing the above description. The scope of the disclosure should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the disclosure should be determined with reference to the appended claims, along with the full scope of equivalents to which such claims are entitled. Further, the limitations of the following claims are not written in means-plusfunction format and are not intended to be interpreted based on 35 U.S.C. § 112, sixth paragraph, unless and until such claim limitations expressly use the phrase "means for" followed by a statement of function void of further structure.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A computer-implemented method for radiotherapy treatment planning, the method comprising:

obtaining data for a radiotherapy treatment of a human subject;

generating a set of radiation controls from the data for the radiotherapy treatment, wherein at least one of the radiation controls is based on a mapping from a continuous computational space;

converting the generated set of radiation controls to a set of treatment delivery parameters, the set of treatment delivery parameters corresponding to capabilities of a radiotherapy treatment machine; and producing treatment plan data for the radiotherapy treatment based on the set of treatment delivery parameters.

2. The method of claim 1, wherein generating the set of radiation controls comprises solving an optimization problem for the radiotherapy treatment.

3. The method of claim 2, wherein optimization variables of the optimization problem comprise a set of auxiliary variables related to at least one of the radiation controls, having a relation defined by a linear operator.

4. The method of claim 2, wherein an objective function of the optimization problem comprises a functional that maps the radiation controls, based on the continuous computational space, into a scalar value.

5. The method of claim 1, wherein generating the set of radiation controls comprises producing a simulation of a radiation dose distribution corresponding to a particular set of radiation controls.

6. The method of claim 5, wherein producing the simulation of the radiation dose distribution corresponding to the particular set of radiation controls comprises applying a transform to produce simulated dose calculations, wherein the transform is defined in the continuous computational space as a convolution.

7. The method of claim 6, wherein applying the transform comprises producing a convolution between a patient-specific dose deposition kernel or fluence deposition matrix and a radiation control corresponding to at least one of irradiation time or radiation intensity.

8. The method of claim 7, wherein each dose deposition kernel or fluence deposition matrix represents a dose rate from a particular sector, a particular collimator, and a particular isocenter, to a particular location in a patient to receive the radiotherapy treatment.

9. The method of claim 6, wherein applying the transform comprises applying a Fourier transform, and wherein the simulated dose calculations are represented as a multiplication in Fourier space.

10. The method of claim 6, wherein applying the transform comprises applying one of a: wavelet, Laplace, Hankel, Mellin, or Hilbert transform.

11. The method of claim 1, wherein converting the generated set of radiation controls to the set of treatment delivery parameters is based on minimizing a degradation of plan quality according to a clinically relevant objective.

12. The method of claim 1, further comprising:

collapsing the set of treatment delivery parameters to a path to perform the radiotherapy treatment, based on a type of the radiotherapy treatment machine.

13. The method of claim 12, wherein the collapsing of the set of treatment delivery parameters is performed using curvelets.

14. The method of claim 1, wherein converting the set of radiation controls to the set of treatment delivery parameters comprises discretizing at least a portion of the set of radiation controls into a set of finite-dimensional treatment delivery parameters.

15. The method of claim 1, wherein generating the set of the radiation controls that belongs to the continuous computational space comprises using a probabilistic language of random fields, performing computations using a finite subset of points, and using interpolation to determine properties of each infinite-dimensional radiation control.

16. The method of claim 1, wherein the data for the radiotherapy treatment comprises imaging data based on a defined two-dimensional or three-dimensional grid.

17. The method of claim 1, wherein the data for the radiotherapy treatment comprises a definition of one or more volumes to receive the radiotherapy treatment from the radiotherapy treatment machine.

18. The method of claim 17, wherein the definition of one or more volumes defines one or more organ at risk areas and one or more target areas.

19. The method of claim 1, wherein the set of radiation controls are based on modulation of radiation using at least one of: focus position, directionality, irradiation time, flux, fluence, energy, or collimation, for the radiation.

20. The method of claim 1, wherein the radiotherapy treatment is provided with a Gamma knife, and wherein the set of treatment delivery parameters comprises a set of isocenters used for delivery of the radiotherapy treatment.

21. The method of claim 20, wherein the set of treatment delivery parameters further comprises timing for delivery of the radiotherapy treatment and a sequence for the delivery of the radiotherapy treatment.

22. The method of claim 1, wherein the radiotherapy treatment is provided with a Volumetric-modulated arc therapy (VMAT) or Intensity modulated radiation therapy (IMRT) using a Linac radiotherapy machine, and wherein the set of treatment delivery parameters comprises a set of arc control points.

23. A non-transitory computer-readable storage medium comprising computer-readable instructions for radiotherapy treatment planning, wherein the instructions, when executed with a computing machine, cause the computing machine to perform operations that:

obtain data for a radiotherapy treatment of a human subject;

generate a set of radiation controls from the data for the radiotherapy treatment, wherein at least one of the radiation controls is based on a mapping from a continuous computational space;

convert the generated set of radiation controls to a set of treatment delivery parameters, the set of treatment delivery parameters corresponding to capabilities of a radiotherapy treatment machine, and produce treatment plan data for the radiotherapy treatment based on the set of treatment delivery parameters.

24. A computing system for radiotherapy treatment planning, the computing system comprising:

one or more memory devices to store data for a radiotherapy treatment of a human subject; and one or more processors configured to perform operations to:

generate a set of radiation controls from the data for the radiotherapy treatment, wherein at least one of the radiation controls is based on a mapping from a continuous computational space;

convert the generated set of radiation controls to a set of treatment delivery parameters, the set of treatment delivery parameters corresponding to capabilities of a radiotherapy treatment machine; and produce treatment plan data for the radiotherapy treatment based on the set of treatment delivery parameters.

\* \* \* \* \*